United States Patent [19]
Bhaskar et al.

[11] 3,943,592
[45] Mar. 16, 1976

[54] TONGUE CLEANING DEVICE

[75] Inventors: Surindar N. Bhaskar, Washington, D.C.; Wayne J. Selting, Omaha, Nebr.; Eleanor L. Gilmore, Seminole, Fla.; Arthur Gross, Silver Spring, Md.

[73] Assignee: The United States of America as represented by the Secretary of the Army, Washington, D.C.

[22] Filed: Nov. 22, 1974

[21] Appl. No.: 526,442

[52] U.S. Cl. .............. 15/160; 15/159 A; 128/304; 128/DIG. 15
[51] Int. Cl.² .................. A46B 9/02; A61B 17/24
[58] Field of Search...... 15/159 A, 160, 187, 210 R; 24/DIG. 18; 128/15, 269, 304, DIG. 15; 132/84 A

[56] References Cited
UNITED STATES PATENTS

| | | |
|---|---|---|
| 1,891,864 | 12/1932 | Barrett................................ 128/304 |
| 3,298,507 | 1/1967 | Micciche..................... 15/159 A UX |
| 3,324,849 | 6/1967 | Kravitz..................................... 128/15 |
| 3,556,667 | 1/1971 | Kaufman........................ 15/118 UX |
| 3,590,414 | 7/1971 | Gores................................. 15/244 R |
| 3,718,009 | 2/1973 | Perina............................. 24/DIG. 18 |
| 3,773,040 | 11/1973 | Gavrilovich................. 128/DIG. 15 |

Primary Examiner—Daniel Blum
Attorney, Agent, or Firm—William G. Gapcynski; Lawrence A. Neureither

[57] ABSTRACT

The invention concerns a device for tongue brushing, the use of which maintains positive oral hygiene and application thereto controls proliferation of plaque forming bacteria and the like. It is the object of this invention to remove from the tongue populations of bacteria and extraneous cellular debris associated with plaque formation, dental caries and gum diseases. A low vertical profile of the device alleviates severe gag reflexes thereby permitting the posterior, dorsal surface of the tongue to be cleaned.

1 Claim, 2 Drawing Figures

TONGUE CLEANING DEVICE

The invention described herein may be manufactured and used by or for the Government for governmental purposes without payment of any royalty thereon.

BACKGROUND OF THE INVENTION

1. Field of the Invention

The invention is in the field of oral physiotherapy. More particularly it concerns a tongue brushing device in which a synthetic tape containing a plurality of flexible hooks is affixed to one end of the flat surface of an elongated member, such as a tongue depressor. The device, when used in brushing the tongue, removes bacterial microorganisms, extraneous cellular debris and the like implicated in plaque formation on dental surfaces.

2. Description of the Prior Art

The dorsum of the tongue is one of the main foci of microorganisms in the oral cavity [B. O. Krasse, Odont. Revy, 5, 203 (1954); D. F. Gordon, Jr. and R. J. Gibbons, Arch. Oral Biol., 11, 627 (1966)]. Many bacterial species resident on the tongue colonize and accumulate in plaque [G. L. Slack and G. H. Bowen, Adv. Fluorine Res., 3, 193 (1965)] and these bacteria are normally integral to dental calculus [A. A. Rizzo, et al., Arch. Oral Biol., 12, 933 (1967)]. Because the tongue is a site of dense bacterial populations and because plaque forms soon after its removal, it appears that the tongue is a source of dental plaque.

The dorsum of the tongue is covered with papillae. The anterior two-thirds of the dorsum is covered with short fungiform papillae while the posterior third is covered with fungiform papillae interspersed with 2 to 3 mm long filiform papillae. Bacteria, food particles and the breakdown products of foods are trapped in the crevices between the papillae, particulary on the posterior third of the dorsum of the tongue. This material is the source of most oral bacteria and mouth order. The tongue, besides harboring large populations of microorganisms, also continuously sheds cells of the surface layer of epithelium. The availability of oral debris from these sources could contribute to plaque formation on dental surfaces [S. E. Jacobson, et al., J. Amer. Dent. Assoc., 87, 134 (1973)].

There has been isolated from natural plaque accumulation on the dental surface the microorganism Streptococcus salivarius which when grown in pure culture (in vitro) deposits plaque layers on sterile, stainless steel wire thus implicating this bacterial microorganism as responsible for natural plaque formation [E. L. Gilmore and S. N. Bhaskar, J. Periodont., 43, 418 (1972)]. Streptococcus salivarius and related species are found in the greatest numbers on the dorsum of the tongue. The degree of reduction in oral debris, as a result of tongue brushing, is directly correlated with the degree of reduction in plaque accumulation [S. E. Jacobson, et al., J. Amer. Dent. Assoc., 87, 134 (1973)].

Numerous devices have been conceived to maintain good oral hygiene and to limit the amount of plaque resident on dental surfaces. The toothbrush in conjunction with dental floss, when used diligently, will remove deposited plaque from tooth surfaces. Water jet devices remove debris from the interdental areas and periodontal sulci and stimulate periodontal tissues. However, these devices do not prevent the formation of plaque and remove only some of the sources of mouth odor. Even when all these methods are successfully employed the patient is assured only of clean tooth surfaces and gingiva [E. L. Gilmore and S. N. Bhaskar, J. Periodont., 43, 418 (1972)].

Toothbrushing is the most frequently used oral hygiene procedure. The recognition of populations of cariogenic bacteria on the tongue led to methods of general oral physiotherapy. Butler [C. E. Butler, Acad. Rev., 12, 64 (1964)] described a tongue brushing routine using a horseshoe-shaped brush with a single row of bristles for the purpose of tongue-oral physiotherapy. The tongue brushing technique for tongue therapy reduces both the size of the incident bacterial population and the extraneous epithelial cells each which can contribute to plaque formation.

SUMMARY OF THE INVENTION

The invention is a tongue brushing device comprised of a tape attached to one end of a flattened, elongated member. The tape contains a high density of flexible hooks precision cut in alternate directions so that when the device, with the hooks contiguous to the tongue's dorsal surface, is applied in a forward motion and vice versa there is removal of cellular debris and the like from that area of the tongue. Tongue parabasal and basal cells are not removed and there is no eliciting of an inflamatory response during the brushing process, therefore allowing safe daily use of the invention. A low vertical profile of the invention alleviates severe gag reflexes thus permitting access to the posterior dorsum of the tongue. The invention is so designed as to be a disposable or reusable product.

It is therefore an object of the present invention to provide a device for maintaining positive oral hygiene which is effective in removing from the tongue cellular debris and the like associated with dental plaque accumulation.

It is a further object of the invention to provide a tongue brushing device having a filamentous hooked fiber design for removal of tongue debris with little downward force on the device thereby alleviating severe gag reflexes.

This device will become increasingly apparent to those skilled in the art by reference to the following description of the invention wherein.

DESCRIPTION OF THE PREFERRED EMBODIMENT

Figure 1:
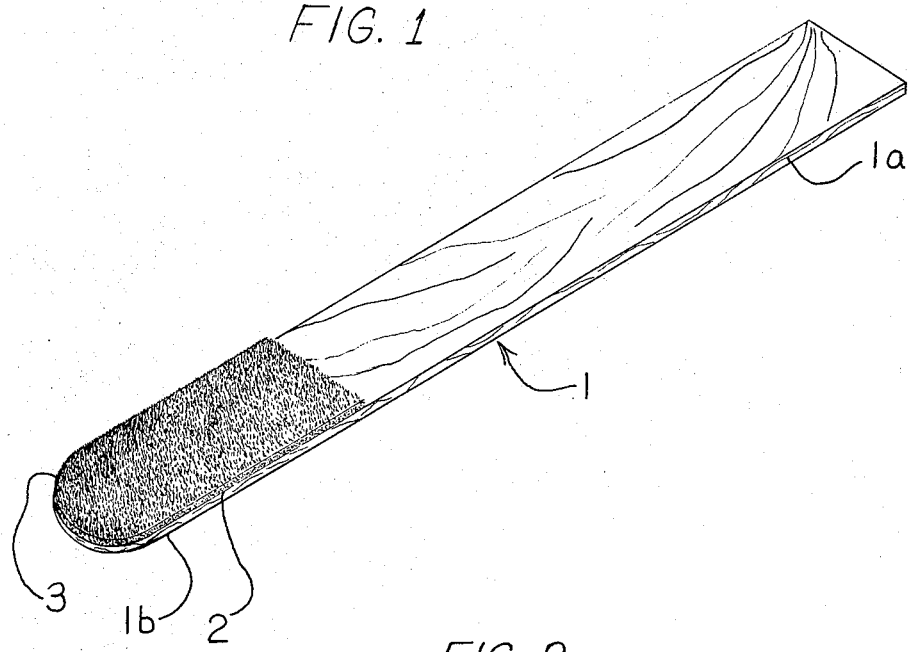
FIG. 1 is a perspective view showing the structure of the tongue brushing device.

Reference is made to FIG. 1 of the drawing wherein the preferred embodiment of the tongue brushing device, shown generally by 1, includes a flat, elongated member, of wood, plastic or the like, whose firm nature functions both as a handle 1a for grasping and as a platform 1b to maintain the base fabric and flexible hooks 3.

Figure 2:
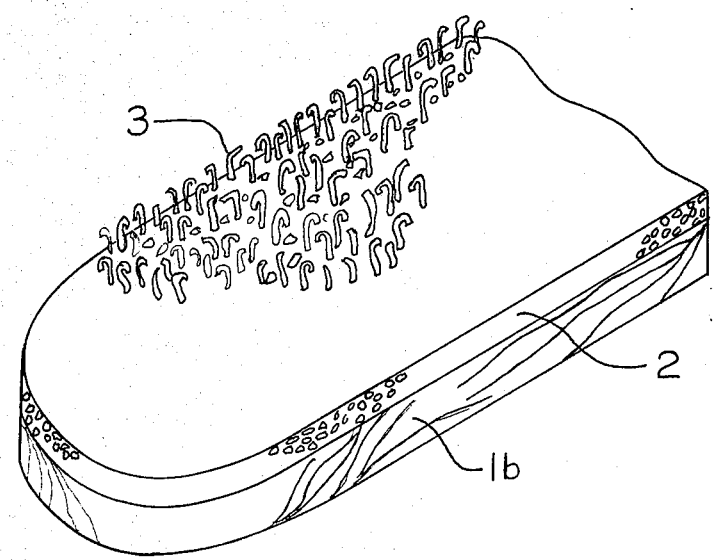
FIG. 2 is an enlarged view of the portion of the tongue brushing device containing the tongue brushing means.

The tape 2, as seen in FIG. 2, is woven of 6.5 mil monofilament nylon in the form of raised and staggered loops. The loops are precision cut in alternate directions and provide a concentration of over 400 hooks, 3, per square inch. The tape is sold commercially as VELCRO Hook Tape No. 65 by Velcro Corp., New York, N.Y., U.S. Pat. Nos. 3,000,384; 3,009,235; 3,076,244; 3,130,111; 3,147,528; 3,154,837; 3,192,589; and 3,387,345. The tape is cemented or otherwise bonded to a flat, elongated member 1b, such as a tongue depressor.

salivarius agar incubated anaerobically at 37°C. Results of these tests are seen in Tables 1 and 2.

TABLE 1

Colony Counts from Habitual Tongue Brushing Subjects*

| Patients | Total Bacterial Count** Brushed | Total Streptococcal Count | | | Total S. salivarius | Salivary Lactobacillus | |
|---|---|---|---|---|---|---|---|
| | | 1 week not Brushed | Brushed | 1 week not Brushed | Brushed | 1 week not Brushed | Organisms/ml |
| $H_1$*** | 68,300 | 1,000,000 | 20,000 | 990,000 | 11,350 | 192,000 | 740,000 |
| $H_2$ | 30,800 | 63,200 | 13,400 | 42,200 | 200 | 2,500 | 400 |
| $H_3$ | 29,250 | 308,600 | 15,000 | 210,000 | 3,150 | 102,700 | 1,820 |
| $H_4$ | 102,700 | 531,700 | 31,000 | 120,000 | 10,400 | 18,200 | 900 |
| $H_5$*** | 117,200 | 191,500 | 90,600 | 106,400 | 13,800 | 21,800 | 1,173,000 |

*An average of counts from three experiments.
**Total bacterial count based on anaerobic growth since these counts were higher than aerobic growth.
***Marked past caries experience.

TABLE 2

Colony Counts from Non-Tongue-Brushing Subjects*

| Patients | Total Bacterial Count** Not Brushed | Total Streptococcal Count | | | Total S. salivarius Not Brushed | Salivary Lactobacillus | |
|---|---|---|---|---|---|---|---|
| | | 1 week Brushed | Not Brushed | 1 week Brushed | | 1 week Brushed | Organisms/ml |
| $NB_1$*** | 244,000 | 171,000 | 138,000 | 84,200 | 42,000 | 52,000 | 120,000 |
| $NB_2$*** | 61,000 | 187,300 | 42,000 | 26,200 | 22,600 | 10,200 | 160,000 |
| $NB_3$*** | 434,000 | 90,000 | 214,000 | 25,800 | 22,000 | 11,200 | 3,200,000 |
| $NB_4$ | 554,000 | 458,000 | 356,000 | 116,000 | 32,000 | 58,000 | 80,000 |
| $NB_5$ | 864,000 | 664,000 | 420,000 | 250,000 | 168,000 | 202,000 | 936,000 |
| $NB_6$ | 137,200 | 152,000 | 29,000 | 30,600 | 200 | 600 | 1,153,000 |

*An average of counts from three experiments.
**Total bacterial count based on anaerobic growth since these counts were higher than aerobic growth.
***Marked past caries experience.

pressor.

The invention has a vertical profile of only 3 mm and provides access to the posterior aspect of the dorsum of the tongue without eliciting the severe gag reflex common to those presently known devices (e.g., toothbrush) used for a like purpose.

The following examples 1, 2, and 3 illustrate the utility of brushing the tongue for maintenance of good oral hygiene and the distinct advantage the present invention has over presently available devices used for a like purpose.

EXAMPLE 1

Bacteriologic Study

Eleven subjects in this investigation were divided into two groups. Group I consisted of five individuals selected on the basis of their habit of habitually brushing the dorsum of the tongue while Group II consisted of six individuals who had not previously brushed the tongue.

The method for tongue cleaning, using a soft nylon brush, consisted of brushing the dorsum of the tongue circumballate papillae forward. If gagging occurred the patient was instructed to use the brush gently and avoid taking it too far posteriorly. A total of eight to 10 strokes were made at each brushing.

Tongue cultures were taken in the morning about 2 hours after breakfast. Each individual was cultured at least 3 times several weeks apart. The two groups then reversed their habits for one week and cultures were again taken as previously described. Appropriate dilutions of the bacterial cultures were plated in duplicate and the counts were averaged to determine total bacterial counts. Total streptococcal and S. salivarius counts represented growth of these colonies on a mitis- Subjects who habitually brushed their tongue (Group I) showed less daily variation in total bacterial and streptococcal counts than nontongue brushers (Group II). Upon cessation of tongue brushing for 1 week, habitual tongue brushers showed a significant rise in total numbers of bacteria.

Following 1 week of tongue brushing, the nontongue brushers usually reduced the total streptococcal count but not necessarily the total bacterial or S. salivarius counts. The reduction in total bacteria and S. salivarius was maintained when proper daily tongue brushing continued beyond 1 week.

EXAMPLE 2

Bacteriologic Study

Eight subjects participated in this study. On day 1, two cultures, one of the left side and another of the right side of the dorsum of the tongue, were taken. Then one-half of the tongue from the midline to the lateral border was cleaned with the present invention (tongue brush) by a dentist, and the participant rinsed his mouth thoroughly. Then another culture of the cleaned side was obtained. The tongue cleaning was performed twice a day for 4 days and once on the 5th day. On the 5th day both sides of the tongue were cultured prior to cleaning and after cleaning a culture was taken from the brushed side only.

The samples from the tongue for microbiological determinations were obtained by pressing 1 $cm^2$ of sterile VELCRO loop tape No. 2,000 on the selected area of the dorsum of the tongue. The square was then immediately placed into a vial of sterile saline and the sample dispersed by homogenization. Serial dilutions in sterile saline were made and aliquots spread on blood agar and mitil-salivarius agar. Also, aliquots were used to prepare pour plates of Veillonella agar. Counts were made from plates showing 30–300 colony forming units and represent a mean of two readings.

Results

Microbiological determination has shown that bacterial counts on the left and right side of the tongue vary greatly. In addition, there were great variations in bacterial concentrations from day to day. While first day results were erratic and inconsistent it was seen that on the 5th day there was a consistent decrease in both anaerobic and aerobic growth after tongue cleaning.

The problem of gagging was alleviated by use of the present invention allowing adequate cleaning of the posterior dorsum of the tongue.

EXAMPLE 3

Cytological Study

Using the same subjects as in EXAMPLE 2, a cytological evaulation was performed. On the fifth day, after taking bacteriological cultures of the tongue, a Papanicolau smear was obtained from both the brushed and nonbrushed sides of the tongue. Two slides were prepared by the Papanicolau method for each side of the tongue. The slides were examined for the presence of:
1. Superficial epithelial cells.
2. Intermediate epithelial cells.
3. Parabasal epithelial cells.
4. Basal epithelial cells.
5. Inflammatory cells.
6. Microorganisms.

The concentration of microbial cells in the smear was graded 1–4 with 4 representing the highest density of bacteria.

Results

Papanicolau smears indicated that in all eight subjects bacterial scores were smaller on the experimental side of the tongue than on the control side. The mean bacterial score of the nonbrushed side of the tongue was 2.9 as compared with 2.1 of the brushed side.

All smears exhibited the presence of superficial and intermediate epithelial cells, but no parabasal, basal epithelial or inflammatory cells could be observed in any of the smears. The device is, therefore, considered safe for daily use.

It was observed during the course of the above studies that caries-inactive individuals within their respective groups appeared to maintain lower streptococcal counts than caries-active individuals. This observation suggests a relationship between numerical bacterial populations of the tongue and plaque formation. It would appear that cleaning of the tongue is a good step, perhaps an essential step, in normal oral hygiene procedures.

The tongue cleaning device of the present invention is superior to the toothbrush normally used for this procedure. The present invention is constructed of a more rigid material than that of the toothbrush. This feature, combined with the unique "hooked" fiber design, allows the removal of debris with less downward force on the device. This design does much to diminish the gag reflex. The device has a low vertical profile, 3 mm compared with 15 mm for a typical toothbrush. This feature also helps limit gagging and allows cleaning of the posterior portions of the dorsum of the tongue. As this area of the tongue has the longest papillae and harbors the most debris and bacteria, its cleaning is essential for maintenance of positive oral hygiene.

As can be seen from the foregoing discussion, the tongue brush device of the present invention provides an effective method for removing bacteria and extraneous cellular debris from the tongue.

We claim:
1. A device to remove bacteria, cellular particulates and the like from the dorsal surface of the tongue comprising a planar, elongated member, filamentous strands disposed to provide a high density per unit area supported on the planar surface at an end portion of said elongated member, wherein the free ends of said strands are hooks which are oriented in random directions and concentrated to provide a density of over 400 hooks per square inch and wherein said elongated member and said filamentous strands in combination have a vertical profile not exceeding 3 millimeters.

* * * * *